(12) United States Patent
Farris

(10) Patent No.: US 7,744,634 B2
(45) Date of Patent: *Jun. 29, 2010

(54) SPINAL ROD SYSTEM

(75) Inventor: Robert A. Farris, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 446 days.

This patent is subject to a terminal disclaimer.

(21) Appl. No.: 10/868,073

(22) Filed: Jun. 15, 2004

(65) Prior Publication Data

US 2005/0277926 A1   Dec. 15, 2005

(51) Int. Cl.
    *A61B 17/70*  (2006.01)
(52) U.S. Cl. ........................................... 606/260
(58) Field of Classification Search ............ 606/60–61, 606/69, 72–73, 258, 261, 279; 403/8, 22, 403/296, 362; 411/393, 422, 423
    See application file for complete search history.

(56) References Cited

U.S. PATENT DOCUMENTS

| | | | |
|---|---|---|---|
| 4,361,141 A | | 11/1982 | Tanner |
| 4,369,770 A | | 1/1983 | Bacal et al. |
| 4,456,005 A | * | 6/1984 | Lichty .......................... 606/60 |
| 4,771,767 A | | 9/1988 | Steffee |
| 4,854,304 A | | 8/1989 | Zielke |
| 5,100,405 A | * | 3/1992 | McLaren ...................... 606/72 |
| 5,154,718 A | | 10/1992 | Cozad et al. |
| 5,167,664 A | * | 12/1992 | Hodorek ....................... 606/73 |
| 5,217,461 A | | 6/1993 | Asher et al. |
| 5,275,600 A | * | 1/1994 | Allard et al. .................. 606/61 |
| 5,330,472 A | | 7/1994 | Metz-Stavenhagen |
| 5,330,474 A | | 7/1994 | Lin |
| 5,336,223 A | | 8/1994 | Rogers |
| 5,403,314 A | | 4/1995 | Currier |
| 5,425,732 A | | 6/1995 | Ulrich |
| 5,486,174 A | | 1/1996 | Fournet-Fayard et al. |
| 5,562,660 A | | 10/1996 | Grob |
| 5,575,790 A | | 11/1996 | Chen et al. |
| 5,593,408 A | | 1/1997 | Gayet et al. |
| 5,605,457 A | * | 2/1997 | Bailey et al. ................ 433/174 |
| 5,630,816 A | | 5/1997 | Kambin |
| 5,643,263 A | * | 7/1997 | Simonson ..................... 606/61 |
| 5,669,910 A | * | 9/1997 | Korhonen et al. ............. 606/61 |
| 5,964,767 A | * | 10/1999 | Tapia et al. ................... 606/73 |
| 6,048,343 A | * | 4/2000 | Mathis et al. ................. 606/72 |

(Continued)

FOREIGN PATENT DOCUMENTS

EP          0 612 507 A1    2/1994

(Continued)

OTHER PUBLICATIONS

CD Horizon Spinal System Surgical Technique, Medtronic Sofamor Danek, Inc., © 2000.

*Primary Examiner*—Eduardo C Robert
*Assistant Examiner*—David Comstock (57) ABSTRACT

A spinal rod system includes a first rod and a second rod engaged to one another in end-to-end fashion. The first and second rods include rod portions with differing characteristics, and a coupling mechanism allows the spinal rod system to be assembled with rod portions having the desired characteristics while minimizing the footprint of the coupling arrangement between the first and second rods.

27 Claims, 4 Drawing Sheets

U.S. PATENT DOCUMENTS

| | | |
|---|---|---|
| 6,099,528 A | 8/2000 | Saurat |
| 6,102,912 A | 8/2000 | Cazin et al. |
| 6,106,527 A | 8/2000 | Wu et al. |
| 6,171,311 B1 * | 1/2001 | Richelsoph .................. 606/61 |
| 6,234,705 B1 * | 5/2001 | Troxell ....................... 403/237 |
| 6,241,730 B1 * | 6/2001 | Alby ............................ 606/61 |
| 6,328,741 B1 | 12/2001 | Richelsoph |
| 6,471,707 B1 * | 10/2002 | Miller et al. .................. 606/73 |
| 6,491,695 B1 * | 12/2002 | Roggenbuck ................ 606/61 |
| 6,602,253 B2 * | 8/2003 | Richelsoph et al. ........... 606/61 |
| 6,613,053 B1 * | 9/2003 | Collins et al. ................. 606/69 |
| 6,673,073 B1 * | 1/2004 | Schafer ....................... 606/61 |
| 6,682,529 B2 * | 1/2004 | Stahurski ..................... 606/61 |
| 6,716,213 B2 * | 4/2004 | Shitoto ........................ 606/61 |
| 6,761,721 B2 * | 7/2004 | Burgess et al. ................ 606/61 |
| 6,783,528 B2 * | 8/2004 | Vincent-Prestigiacomo .. 606/61 |
| 6,875,211 B2 * | 4/2005 | Nichols et al. ................ 606/61 |
| 2004/0092931 A1 * | 5/2004 | Taylor et al. ................. 606/61 |
| 2004/0153067 A1 * | 8/2004 | Smith et al. .................. 606/60 |
| 2005/0090821 A1 * | 4/2005 | Berrevoets et al. ........... 606/61 |
| 2005/0228376 A1 * | 10/2005 | Boomer et al. ................ 606/61 |
| 2005/0228377 A1 * | 10/2005 | Chao et al. ................... 606/61 |

FOREIGN PATENT DOCUMENTS

EP     0 584 803 A1     3/1994

* cited by examiner

SPINAL ROD SYSTEM

BACKGROUND

The spine is subject to various pathologies that compromise its load bearing and support capabilities. Such pathologies of the spine include, for example, degenerative diseases, the effects of tumors and, of course, fractures and dislocations attributable to physical trauma. In the treatment of diseases, malformations or injuries affecting spinal motion segments (which include two or more adjacent vertebrae and the disc tissue or disc space therebetween), and especially those affecting disc tissue, it has long been known to remove some or all of a degenerated, ruptured or otherwise failing disc. It is also known that artificial discs, fusion implants, or other interbody devices can be placed into the disc space after disc material removal. External stabilization of spinal segments alone or in combination with interbody devices also provides advantages. Elongated rigid plates, rods and other external stabilization devices have been helpful in the stabilization and fixation of a spinal motion segment, in correcting abnormal curvatures and alignments of the spinal column, and for treatment of other conditions.

While external rod systems have been employed along the vertebrae, the geometric and dimensional features of these rod systems and patient anatomy constrain the surgeon during surgery and prevent optimal placement and attachment along the spinal column. For example, elongated, one-piece rods can be difficult to maneuver into position along the spinal column, and also provide the surgeon with only limited options in sizing and selection of the rod system to be placed during surgery.

SUMMARY

In one aspect, a rod system having a first rod attachable to a second rod in end-to-end fashion allows the surgeon to select from rods having various dimensions and/or other characteristics to construct a rod system that is optimal for pre-operative planning and to address conditions encountered during surgery. The end-to-end attachment minimizes the intrusiveness of the rod system into the anatomy adjacent the connection location.

In another aspect, a rod system includes a first rod attachable to a second rod in end-to-end fashion includes a coupling mechanism that axially and torsionally constrains the first and second rods to one another.

In a further aspect, a rod system includes a first rod attachable to a second rod in end-to-end fashion with a coupling mechanism. The coupling mechanism includes a coupling body on one rod that axially receives a coupling member on the other rod and engagement of the coupling member with the coupling body axially constrains the first and second rods to one another.

In another aspect, a method for assembling a spinal rod system includes: providing a first spinal rod with a first rod portion for attachment to the spinal column, said first rod portion including a first characteristic and a coupling member at an end of the rod portion; providing a second spinal rod with a second rod portion for attachment to the spinal column, said second rod portion including a second characteristic and a coupling body at an end of the rod portion; and axially constraining the first spinal rod to the second spinal rod with the coupling member engaging the coupling body and the first and second spinal rods centered along a longitudinal axis of the spinal rod system.

DESCRIPTION OF THE ILLUSTRATED EMBODIMENTS

For the purposes of promoting an understanding of the principles of the invention, reference will now be made to the embodiments illustrated in the drawings and specific language will be used to describe the same. It will nevertheless be understood that no limitation of the scope of the invention is hereby intended. Any such alterations and further modifications in the illustrated devices, and any such further applications of the principles of the invention as illustrated herein being contemplated as would normally occur to one skilled in the art to which the invention relates.

Figure 1:
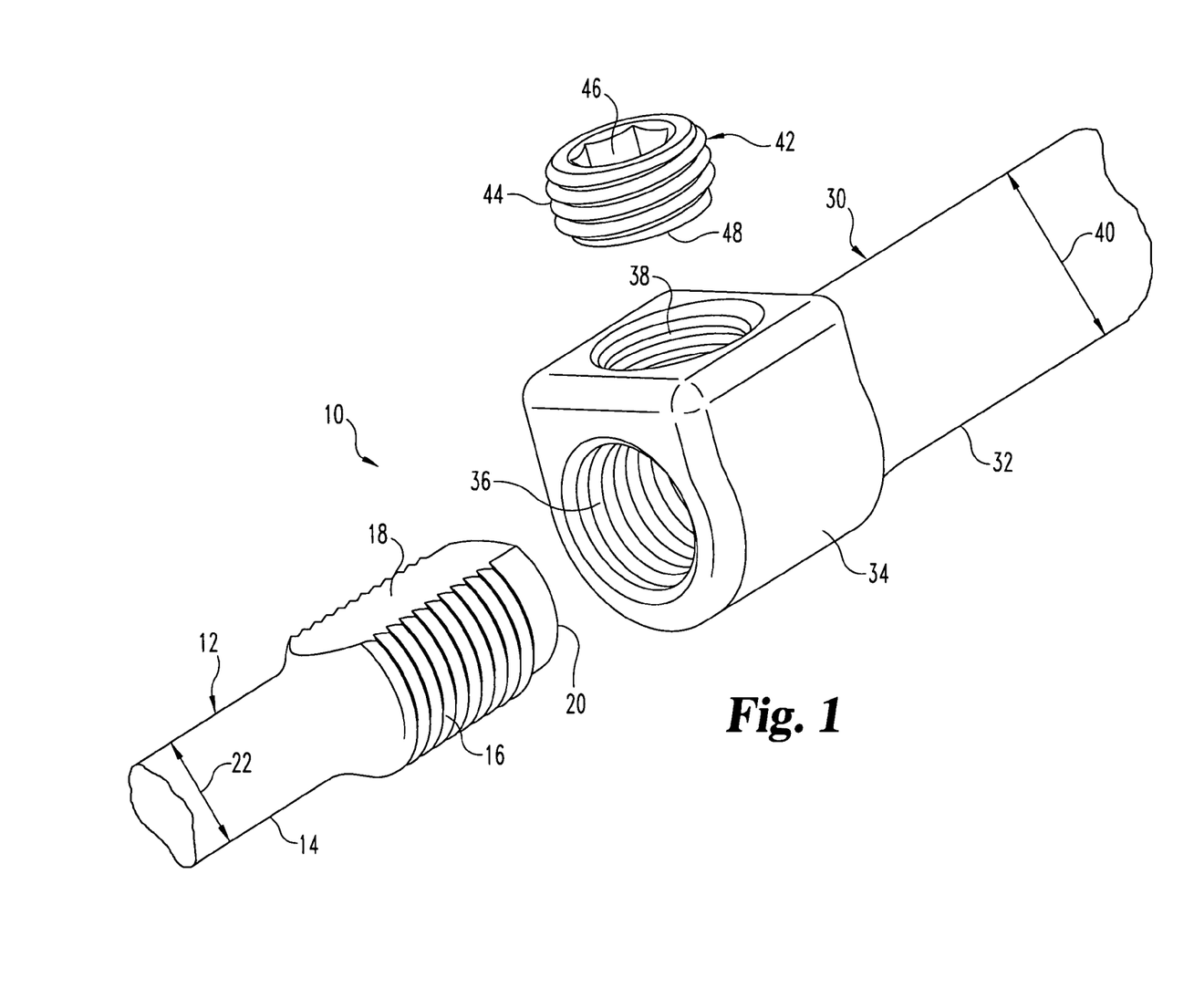
FIG. 1 is an exploded perspective view of a portion of one embodiment rod system.

In FIG. 1 there is shown a spinal rod system 10 including a first rod 12 and a second rod 30. First rod 12 and second rod 30 are releasably coupled to one another in end-to-end fashion with a coupling mechanism 28. Coupling mechanism 28 includes a coupling body on one of the first and second rods 12, 30 and a coupling member on the other of the first and second rods 12, 30. The coupling mechanism 28 is configured to secure rods 12, 30 to one another in end-to-end fashion. This minimizes the footprint or intrusiveness of the coupling mechanism into the tissue surrounding the rod system, and maximizes the length of the rod portion of each rod available for positioning and/or attachment along the spinal column.

Figure 5:
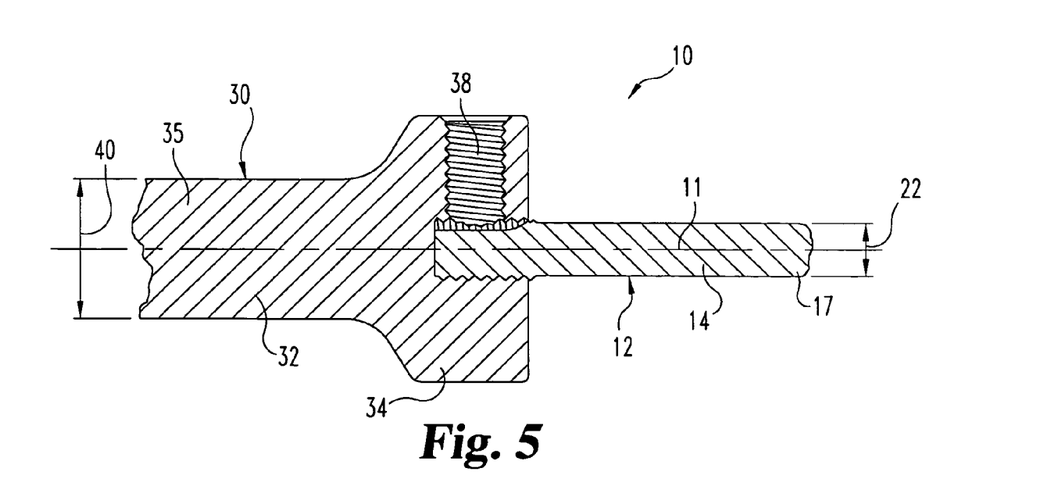
FIG. 5 is a section view of the rod system of FIG. 1 assembled with the engaging member removed from the coupling mechanism.

First rod 12 includes a first rod portion 14 and coupling member 16 at a first end of first rod portion 14. Rod portion 14 extends from coupling member 16 to an opposite second end 17 (FIG. 5.) Second rod 30 includes coupling body 34 at a first end thereof. Rod portion 32 extends from coupling body 34 to an opposite second end 35 (FIG. 5.) One or both of the second ends 17, 35 of rod portions 14, 32 may include a coupling member, a coupling body, or simply provide a terminal end shaped like the corresponding rod portion 14, 32 as shown. Although only one coupling mechanism 28 is shown, one or more of the rods 12, 30 can be adapted for engagement with another rod at each end thereof so that three or more rods may comprise the rod system. Rod portions 14, 32 can be secured to vertebrae of the spinal column system with any one or combination of hooks, screws, bolts, multi-axial screws, staples, cables or wires, sutures, clamps, interbody fusion devices, an implant between vertebrae, and/or other attachment devices and systems.

First rod portion 14 can be provided with a characteristic that differs from a characteristic of second rod portion 32. The coupling mechanism 28 allows rods of differing characteristics to be secured to one another in end-to-end fashion to provide a rod system that is adapted for the anatomy, surgical condition, or surgical procedure. In one embodiment, the characteristic includes a cross-sectional dimension of the rod portions 14, 32. Other embodiments contemplate selection criteria for selection and assembly of the rod portion to include any one or combination of characteristics, including length, contouring, flexibility, surface features, shape, section modulus, elasticity, materials and material properties, and coatings, for example.

Figure 2:
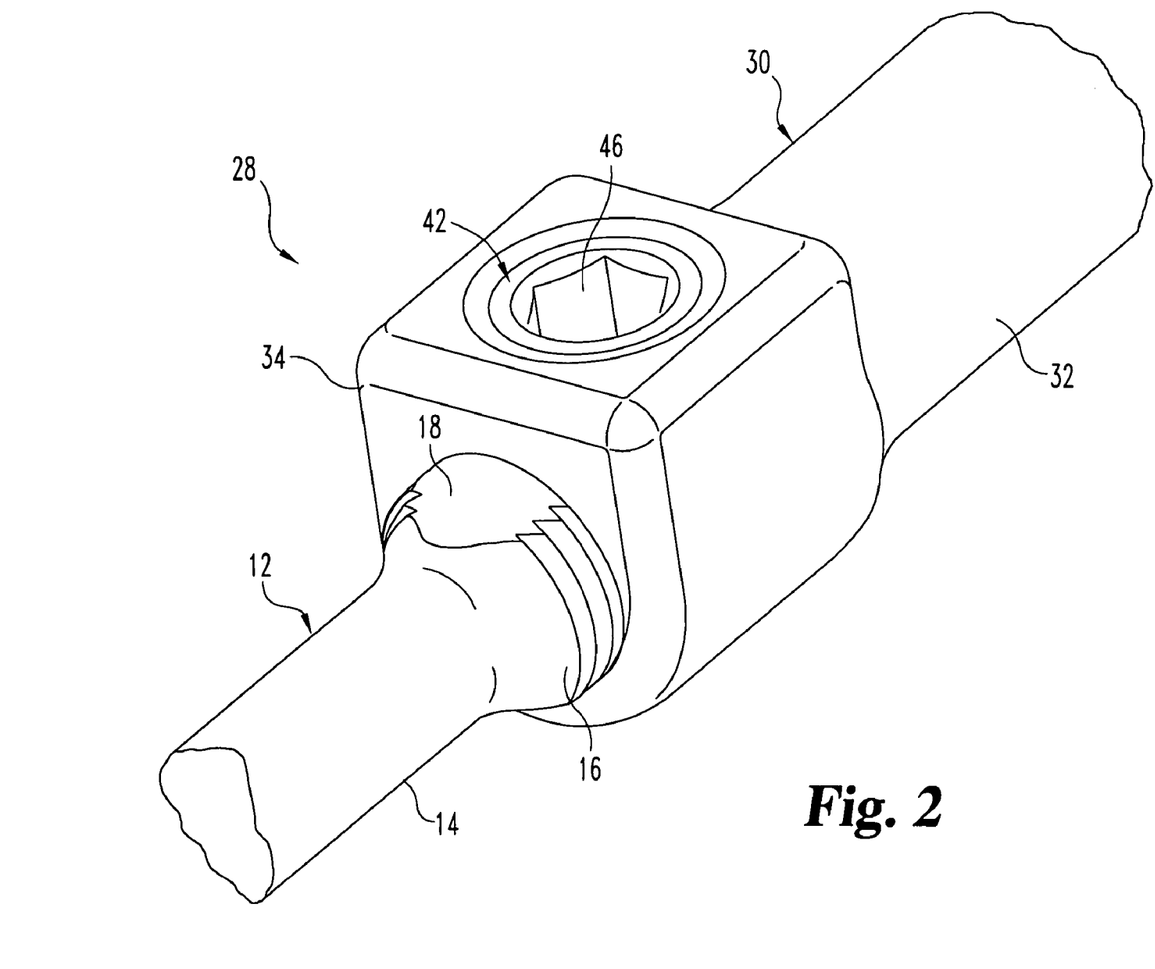
FIG. 2 is a perspective view of the rod system of FIG. 1 assembled.

As shown in FIGS. 1-2 and 5, rod portion 14 extends along longitudinal axis 11 and includes a first cross-sectional dimension 22 between opposite sides thereof transverse to longitudinal axis 11. Similarly, rod portion 32 extends along longitudinal axis 11 and includes a second cross-sectional dimension 40 between opposite sides thereof transverse to longitudinal axis 11. In the illustrated embodiment, cross-sectional dimension 22 corresponds to a diameter of a cylindrical rod portion 14 that is smaller than a diameter corresponding to cross-sectional dimension 40 of a cylindrical rod portion 32. In one specific application, the diameter of first rod portion 14 is sized to extend along a first portion of the spine, such as the cervical region, and the diameter of second rod portion 32 is sized to extend along a second portion of the spine, such as the thoracic region. Other systems contemplate multiple rod portions coupled to one another in end-to-end fashion with characteristics adapted for positioning along any one or combination of the sacral, lumbar, thoracic and cervical regions of the spinal column.

Figure 3:
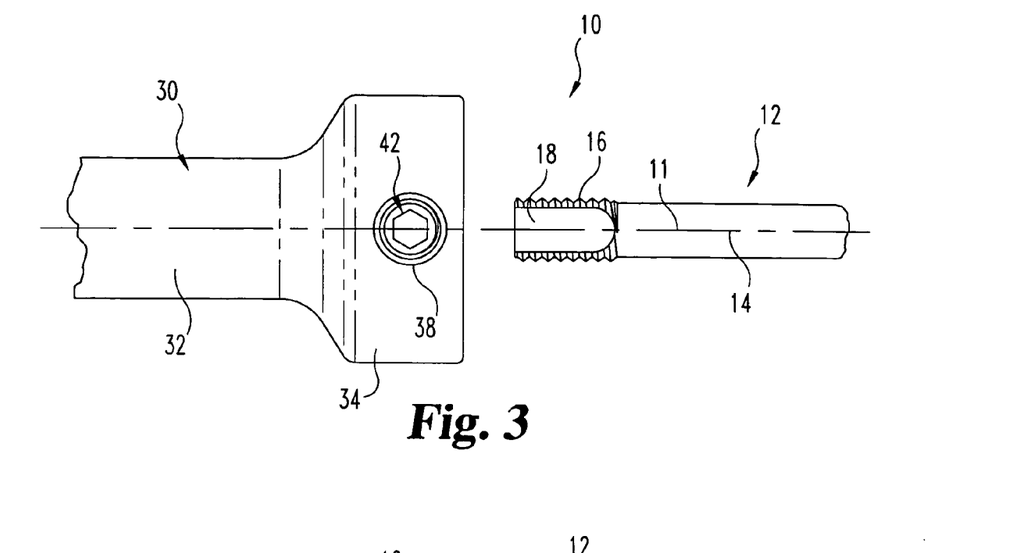
FIG. 3 is an exploded elevational view of the rod system of FIG. 1.
Figure 4:
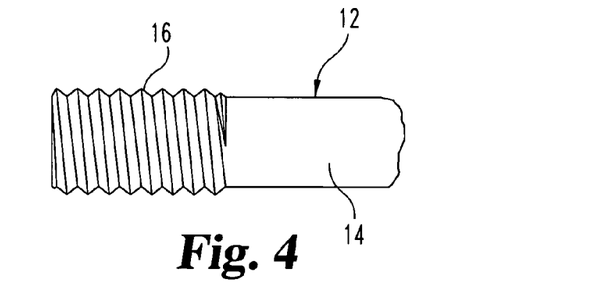
FIG. 4 is a view of a first rod rotated 180 degrees about its longitudinal axis from its FIG. 3 orientation.

Coupling member 16 includes a threaded outer surface extending from rod portion 14 to an end member 20 lacking threads. Coupling member 16 further includes a contact portion 18 along at least one side thereof, as also shown in FIG. 3. Contact portion 18 can be formed by a cutout providing a flat surface extending along coupling member 16. Contact portion 18 can also include a concave surface, a convex surface, a receptacle, or other suitable configuration for contacting an engaging member. As shown in FIG. 5, the thread pattern of coupling member 16 extends completely therearound between the opposite sides of contact portion 18. Other embodiments contemplate that multiple contact portions are provided along coupling member 16 to provide multiple engagement locations for engaging member 42, as discussed further below.

Coupling body 34 can be enlarged relative to rod portion 32 to provide a flange or hub to which coupling member 16 can be releasably engaged. In the illustrated embodiment, coupling body 34 is a cubic block, although other shapes are also contemplated, such as rectangular and cylindrical shapes. Coupling body 34 includes a first bore 36 formed internally therein that extends along and opens along longitudinal axis 11 at an end of coupling body 34. Coupling body 34 further includes a second bore 38 extending therein transversely to first bore 36. As further shown in FIG. 5, second bore 38 can be internally threaded for receipt of an engagement member. Second bore 38 can also be orthogonal to first bore 36, although other orientations are also contemplated.

As shown in FIGS. 2 and 5, rods 12, 30 can be assembled in end-to-end fashion and aligned along longitudinal axis 11 with coupling member 16 received in bore 36 and axially constrained by threaded engagement with coupling body 34. End member 20 facilitates positioning and alignment of coupling member 16 in bore 36, preventing or reducing the possibility of cross-threading coupling member 16 with coupling body 34. The axial load between rods 12, 30 is carried by the engagement between coupling member 16 and coupling body 34, which are also aligned along the axis 11 of rod system 10 when engaged. Accordingly, torsional loading of the components of rod system 10 is minimized since the rods 12, 30 are connected to one another in end-to-end fashion along axis 11. Furthermore, the footprint of coupling mechanism 28 both transversely to rods 12, 30 and along rods 12, 30 is minimized, making the procedure for positioning rod system 10 less invasive, providing additional rod length for contouring and attachment of fasteners for engagement with the spinal column, and minimizing the number of components employed in securing the rods 12, 30 to one another.

Engaging member 42 is positionable in second bore 38 and engageable to coupling member 16 to prevent rod 12 from disengaging from rod 30. In one embodiment, contact portion 18 of coupling member 16 is oriented toward second bore 38, and engaging member 42 is an externally threaded set screw 44 engageable in second bore 38. A tool engaging recess 46 is provided for engagement with a tool, such as a hex driver, to allow the set screw 44 to be driven into second bore 38. Set screw 44 is driven into second bore 38 so that end 48 is in contact with contact portion 18, preventing coupling member 16 from rotating in body 30 and resisting torsional loading between rods 12, 30.

With contact surface 18 aligned with bore 38, the rod portions 14, 32 are oriented in a predetermined alignment with one another determined by the location of contact surface 18 and bore 38 relative to the respective rod portions 14, 32. For example, if one or both of rod portions 14, 32 are provided with non-circular cross-sections, through-holes, or other characteristic along their respective lengths, the characteristics can be oriented relative to contact surface 18 and/or bore 38 so that when contact surface 18 is engaged by engaging member 42, the characteristic of rod portion 14 is positioned in a desired alignment relative rod portion 32. In this manner, the rod portions 14, 32 can be secured with these characteristics in a predetermined alignment relative to one another, and maintained in this alignment by the engagement of engaging member 42 with contact surface 18.

Other embodiments contemplate other arrangements for coupling mechanism 28. For example, engaging member 42 can be a pin that is received in a hole or recess in coupling member 16. Coupling body 34 can be a nut rotatably captured on the end of rod portion 32. Coupling mechanism 28 can include a bayonet locking type device, or a spring-biased ball plunger in coupling member 16 that is received in a detent in coupling body 34.

Figure 6:
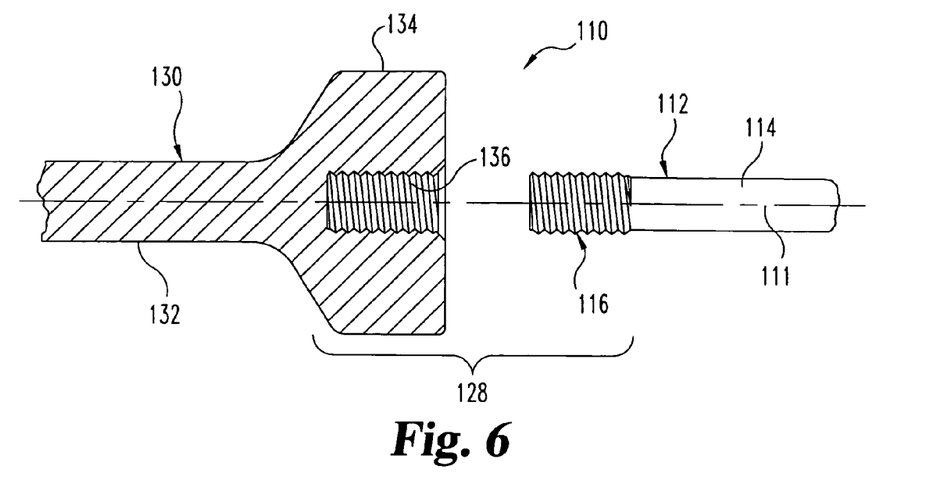
FIG. 6 is an exploded elevation view in partial section of another embodiment rod system.

In FIG. 6, there is shown another embodiment rod system 110 extending along a longitudinal axis 111 and including a first rod 112 having rod portion 114 and coupling member 116. A second rod 130 includes rod portion 132 and a coupling body 134 with an axial bore 136. First and second rod portions 114, 132 can be provided with differing characteristics and axially constrained to one another in end-to-end fashion. Body 130 does not include a second bore for an engaging member, and coupling member 116 can be provided completely threaded therearound. To torsionally constrain coupling member 116 in coupling body 134, coupling member 116 can be provided with locking threads to prevent first and second rods 112, 130 from rotating relative to one another. In another embodiment, a simple threaded engagement is provided to axially constrain rods 112, 130 to one another, and relative rotation of rods 112, 130 is resisted by the engagement of rods 112, 130 to the spinal column.

Figure 7:
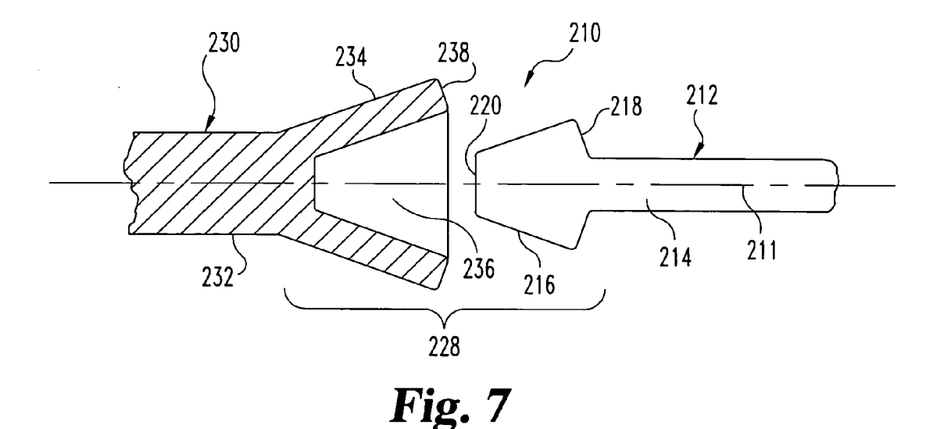
FIG. 7 is an exploded elevation view in partial section of another embodiment rod system.

In FIG. 7, there is shown another embodiment rod system 210 including a first rod 212 and a second rod 230 extending along a longitudinal axis 211. First rod 212 includes a first rod portion 214 and second rod 230 includes a second rod portion 232. First and second rod portions 214, 232 can be provided with differing characteristics and attached to one another in end-to-end fashion with a coupling mechanism 228. First rod 212 includes a coupling member 216 at an end of rod portion 214. Coupling member 216 is externally tapered toward the first end 220 of rod 212, and forms a lip 218 extending about rod portion 214. Coupling body 234 includes an axial bore that is tapered from a first end 238 of second rod 230 toward rod portion 232. Engaging member 216 is press fit into bore 236 so that the tapered outer surface is received in the flared bore to frictionally engage and axially and torsionally constrain first rod 212 to second rod 230 in end-to-end fashion. It is further contemplated that an engaging member can be provided extending between coupling body 234 and coupling member 216 to provide additional fixation in addition to the friction fit between coupling body 234 and coupling member 216.

Figure 8:
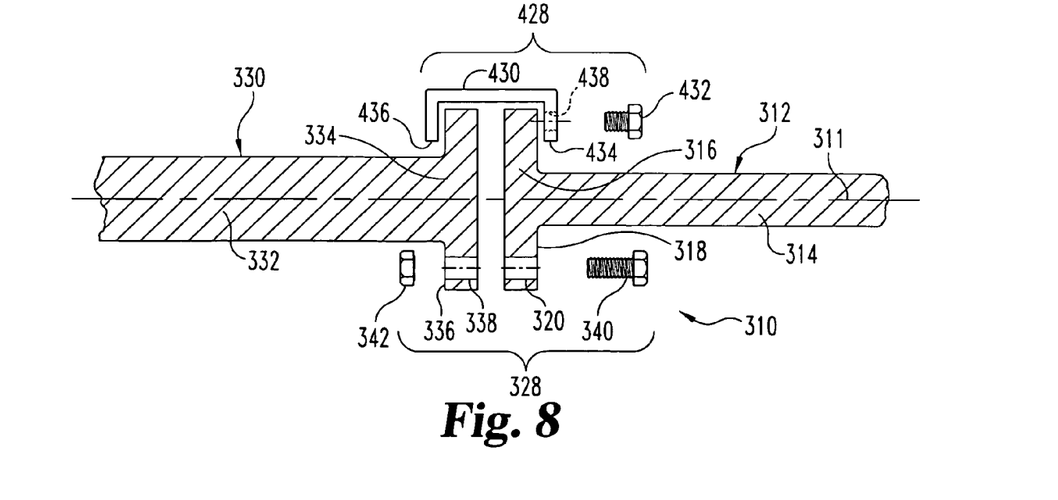
FIG. 8 is an exploded elevation view of another embodiment rod system with two embodiments of a coupling mechanism for coupling the rods to one another.

In FIG. 8, there is shown another embodiment rod system 310 including a first rod 312 and a second rod 330 extending along longitudinal axis 311. First rod 312 includes a first rod portion 314 and second rod 330 includes a second rod portion 332. First rod 312 includes a coupling member at an end of rod portion 314 in the form of a flange or hub 316 extending around first rod portion 314. Flange 316 forms a lip 318 extending about rod portion 314. Second rod 330 includes a coupling body at an end thereof that is also in the form of a flange or hub 334. Flange 334 extends around and forms a lip 336 about second rod portion 332. Flanges 316, 334 are positionable in abutting engagement with one another in end-to-end fashion so that rods 312, 330 having differing characteristics can be secured to one another to provide rod system 310.

Coupling mechanism 328 includes a fastener 340 extendable through aligned bores 320, 338 extending parallel to axis 311 through the flanges 316, 334. A nut 342 is engageable with fastener 340 to axially constrain rods 312, 330 together in end-to-end fashion. It is contemplated that a number of fasteners can be positioned about the flanges to provide additional axial constraint and also torsional constraint to rods 312, 330. Although fastener 340 has been shown as a bolt with a nut, other fasteners are also contemplated, including rivets, screws, and bolts threadingly engaged to the flange bores, for example.

Another embodiment coupling mechanism 428 is shown in FIG. 8 that includes a clamping member 430 and an engaging member 432. Clamping member 430 includes arms 434, 436 at opposite ends thereof that extend along adjacent ones of the flanges 316, 334. Fastener 432 extends parallel to axis 311 and is engageable to a bore 438 in arm 434. Fastener 432 is positionable in contact with flange 316 to bias arm 436 into contact with flange 334. Flanges 316, 334 are drawn toward one another to position the flanges in end-to-end contact and axially constrain rods 312, 330 relative to one another. It is contemplated that a number of clamping members can be provided about flanges 316, 334 to provide a secure clamping arrangement to prevent rods 312, 330 from pivoting or splaying relative to one another. It is further contemplated that clamping member 430 can be sized to extend along a portion of the perimeter of flanges 316, 334, and a number of fasteners 432 are provided to clamp first and second rods 312, 330 to one another.

While the invention has been illustrated and described in detail in the drawings and foregoing description, the same is to be considered as illustrative and not restrictive in character. All changes and modifications that come within the spirit of the invention are desired to be protected.

What is claimed is:

1. A spinal rod system, comprising:
a first elongated rod extending along a longitudinal axis between a first end and an opposite second end, said first rod including a first rod portion with a length sized for attachment between vertebrae and a first characteristic corresponding at least to a first cross-sectional dimension between opposite sides of said first rod portion;
a second elongated rod extending along a longitudinal axis between a first end and an opposite second end, said second rod including a second rod portion with a length sized for attachment between vertebrae and a second characteristic corresponding at least to a second cross-sectional dimension between opposite sides of said second rod portion; and
a coupling mechanism for releasably coupling said first ends of said first and second rods in end-to-end fashion and said opposite sides of each of said first and second rod portions aligned with one another and extending from said coupling mechanism in opposite directions from one another, wherein one of said aligned first and second cross-sectional dimensions is less than the other of said aligned first and second cross-sectional dimensions, wherein one of said first and second rods includes a coupling member at an end thereof, said coupling member including an external thread pattern interrupted by a flattened surface portion extending along said coupling member.

2. The system of claim 1, wherein said coupling mechanism axially and torsionally constrains said first and second rods relative to one another.

3. The system of claim 1, wherein said first and second cross-sectional dimensions correspond to a diameter of respective ones of said first and second rod portions.

4. The system of claim 1, wherein said coupling mechanism includes an engaging member positionable in engagement with said surface portion to resist rotation of said coupling member relative to a coupling body at said first end of the other of said first and second rods.

5. The system of claim 1, wherein said coupling mechanism includes a coupling body adjacent one of said first ends and a coupling member adjacent the other of said first ends, said coupling member being releasably engageable to said coupling body to couple said first ends to one another in end-to-end fashion.

6. The system of claim 5, wherein said coupling body includes an internally threaded first bore and said coupling member is externally threaded for removable engagement in said first bore.

7. The system of claim 5, wherein said coupling body is enlarged relative to said rod portion of the respective one of the first and second rods on which said coupling body is located.

8. The system of claim 1, wherein said first rod portion and said second rod portion each include a circular cross-section along said respective rod portion and said first and second cross-sectional dimensions each correspond to a diameter of said respective rod portion.

9. A spinal rod system, comprising:
a first elongated rod extending along a longitudinal axis between a first end and an opposite second end, said first rod including a first rod portion with a length sized for attachment between vertebrae and a first characteristic corresponding at least to a first cross-sectional dimension between opposite sides of said first rod portion;
a second elongated rod extending along a longitudinal axis between a first end and an opposite second end, said second rod including a second rod portion with a length sized for attachment between vertebrae and a second characteristic corresponding at least to a second cross-sectional dimension between opposite sides of said second rod portion;

a coupling mechanism for releasably coupling said first ends of said first and second rods in end-to-end fashion and said opposite sides of each of said first and second rod portions aligned with one another and extending from said coupling mechanism in opposite directions from one another, wherein one of said aligned first and second cross-sectional dimensions is less than the other of said aligned first and second cross-sectional dimensions, wherein:

said coupling mechanism includes a coupling body adjacent one of said first ends and a coupling member adjacent the other of said first ends, said coupling member being releasably engageable to said coupling body to couple said first ends to one another in end-to-end fashion;

said coupling body includes an internally threaded first bore and said coupling member is externally threaded for removable engagement in said first bore; and said externally threaded coupling member includes a partially cylindrical body with a flattened surface on at least one side thereof along said external threads.

10. The system of claim 9, wherein said flattened surface lacks threads.

11. The system of claim 10, wherein said coupling body includes a second bore transversely oriented to and intersecting said first bore, said second bore including an internal thread for engaging an externally threaded set screw, said set screw positionable in engagement with said flattened surface of said coupling member when said coupling member is engaged in said first bore to prevent said coupling member from rotating in said first bore and to align said opposite sides of said first and second rod portions with one another.

12. The system of claim 11, wherein said second bore is orthogonal to said first bore.

13. A spinal rod system, comprising:

a first elongated rod extending along a longitudinal axis between a first end and an opposite second end, said first rod including a first rod portion with a length sized for attachment between vertebrae and a first characteristic corresponding at least to a first cross-sectional dimension between opposite sides of said first rod portion;

a second elongated rod extending along a longitudinal axis between a first end and an opposite second end, said second rod including a second rod portion with a length sized for attachment between vertebrae and a second characteristic corresponding at least to a second cross-sectional dimension between opposite sides of said second rod portion;

a coupling mechanism for releasably coupling said first ends of said first and second rods in end-to-end fashion and said opposite sides of each of said first and second rod portions aligned with one another and extending from said coupling mechanism in opposite directions from one another, wherein one of said aligned first and second cross-sectional dimensions is less than the other of said aligned first and second cross-sectional dimensions, wherein:

said coupling mechanism includes a coupling body adjacent one of said first ends and a coupling member adjacent the other of said first ends, said coupling member being releasably engageable to said coupling body to couple said first ends to one another in end-to-end fashion; and said coupling body includes an internal bore flared toward said respective adjacent first end, and said coupling member includes an outer surface tapering toward said respective other adjacent first end, said flared bore receiving said tapered body in frictional engagement to releasably couple said first and second rods in end-to-end fashion.

14. A spinal rod system, comprising:

a first elongated rod extending along a longitudinal axis between a first end and an opposite second end, said first rod including a first rod portion with a length sized for attachment between vertebrae and a first characteristic corresponding at least to a first cross-sectional dimension between opposite sides of said first rod portion;

a second elongated rod extending along a longitudinal axis between a first end and an opposite second end, said second rod including a second rod portion with a length sized for attachment between vertebrae and a second characteristic corresponding at least to a second cross-sectional dimension between opposite sides of said second rod portion;

a coupling mechanism for releasably coupling said first ends of said first and second rods in end-to-end fashion and said opposite sides of each of said first and second rod portions aligned with one another and extending from said coupling mechanism in opposite directions from one another, wherein one of said aligned first and second cross-sectional dimensions is less than the other of said aligned first and second cross-sectional dimensions, wherein:

said coupling mechanism includes a coupling body adjacent one of said first ends and a coupling member adjacent the other of said first ends, said coupling member being releasably engageable to said coupling body to couple said first ends to one another in end-to-end fashion; and each of said coupling body and said coupling member includes a flange extending radially about the respective rod portion of the first and second rods.

15. The system of claim 14, wherein said coupling mechanism further comprises at least one fastener positionable through bores extending through the respective flanges.

16. The system of claim 15, wherein said fastener extends parallel to the longitudinal axes of said first and second rod portions.

17. The system of claim 14, wherein said coupling mechanism further comprises a clamp positionable about said flanges and engageable thereto to clamp said flanges to one another.

18. A spinal rod system, comprising:

a first elongated rod extending along a longitudinal axis between a first end and an opposite second end, said first rod including a rod portion with a length sized for attachment between vertebrae of the spinal column and a first characteristic and a coupling member at said first end; and a second elongated rod extending along said longitudinal axis between a first end and an opposite second end, said second rod including a rod portion with a length sized for attachment between vertebrae of the spinal column and a second characteristic and a coupling body at said first end, said coupling body including a bore extending along said longitudinal axis, wherein said first and second rods are releasably engageable to one another in end-to-end fashion with said coupling member received in and axially fixed relative to said coupling body by engagement with said coupling body in said bore of said coupling body and said first and second rod portions extending from said coupling member and said coupling body in opposite directions from one another, wherein said first bore of said coupling body is internally threaded and said coupling member is externally threaded for engagement in said first bore and said externally threaded coupling member includes a flattened portion extending along said threads.

19. The system of claim 18, wherein the first and second characteristics each include a diameter of a respective one of the first and second rod portions, wherein the diameter of the first rod is less than the diameter of the second rod.

20. The system of claim 18, wherein said first bore of said coupling body is internally threaded and said coupling member is externally threaded for engagement in said first bore.

21. The system of claim 18, wherein said flattened portion lacks threads.

22. The system of claim 21, wherein said coupling body includes a second bore transversely oriented to and intersecting said first bore, said second bore including an internal thread profile for engaging a fastener, said fastener positionable in engagement with said cutout portion of said coupling member when said coupling member is engaged in said first bore to prevent said coupling member from rotating in said first bore.

23. The system of claim 22, wherein said second bore is orthogonal to said first bore.

24. The system of claim 18, wherein said coupling body is enlarged relative to said rod portion of the respective one of the first and second rods on which said coupling body is located.

25. The system of claim 18, wherein said first and second characteristics of said first and second rod portions is a circular cross-section along a length of each of said rod portions, wherein a diameter of one of said rod portions is less than a diameter of the other of said rod portions along said lengths.

26. The system of claim 18, wherein said rod portion of said first rod includes a first configuration and said coupling member includes a second configuration different from said first configuration.

27. A spinal rod system, comprising:
 a first elongated rod extending along a longitudinal axis between a first end and an opposite second end, said first rod including a rod portion with a length sized for attachment between vertebrae of the spinal column and a first characteristic and a coupling member at said first end; and
 a second elongated rod extending along said longitudinal axis between a first end and an opposite second end, said second rod including a rod portion with a length sized for attachment between vertebrae of the spinal column and a second characteristic and a coupling body at said first end, said coupling body including a bore extending along said longitudinal axis, wherein said first and second rods are releasably engageable to one another in end-to-end fashion with said coupling member received in and axially fixed relative to said coupling body by engagement with said coupling body in said bore of said coupling body and said first and second rod portions extending from said coupling member and said coupling body in opposite directions from one another, wherein said coupling body includes an internal bore flared toward said respective first end, and said coupling member includes a tapered outer surface tapering toward said respective first end, said flared bore receiving said tapered body in frictional engagement to releasably couple said first and second rods in end-to-end fashion.

* * * * *